US00PP37313P2

(12) United States Plant Patent
Rietberg

(10) Patent No.: US PP37,313 P2
(45) Date of Patent: Mar. 10, 2026

(54) ***CHAMAECYPARIS* PLANT NAMED 'Edengra 23'**

(50) Latin Name: *Chamaecyparis lawsoniana*
Varietal Denomination: Edengra 23

(71) Applicant: Henrik Christiaan Cozijn Rietberg, Wezep (NL)

(72) Inventor: Henrik Christiaan Cozijn Rietberg, Wezep (NL)

(73) Assignee: EDENS CREATIONS BV, Wezep (NL)

( * ) Notice: Subject to any disclaimer, the term of this patent is extended or adjusted under 35 U.S.C. 154(b) by 0 days.

(21) Appl. No.: 19/315,655

(22) Filed: Sep. 1, 2025

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 5/00; A01H 5/12; A01H 7/00
See application file for complete search history.

(56) References Cited

PUBLICATIONS

Plantarium Groen-Direkt retrieved on Oct. 22, 2025 at https://plantariumgroendirekt.nl/nieuwigheden-en/chamaecyparis-lawsoniana-edengra23-ellgrandii/?lang=en, 2 pp. (Year: 2025).*
UPOV Pluto Plant Variety Database 20251022 retrieved on Oct. 22, 2025 at https://plluto.upov.int/result, one page. (Year: 2025).*

* cited by examiner

*Primary Examiner* — June Hwu
(74) *Attorney, Agent, or Firm* — Penny J. Aguirre

(57) ABSTRACT

A new cultivar of *Chamaecyparis* plant named 'Edengra 23' that is characterized by its upright, columnar and compact plant habit, its foliage that is thick and coarse in texture, and its very good growth in peat-free soil.

3 Drawing Sheets

Botanical classification: *Chamaecyparis lawsoniana.*
Varietal denomination: 'Edengra 23'.

CROSS REFERENCE TO A RELATED APPLICATION

This application is related to a European plant breeders' rights application filed on Nov. 15, 2023, application No. 2023/2360. The information for the plant breeders' rights application was received directly from the Inventor.

BACKGROUND OF THE INVENTION

The present invention relates to a new and distinct cultivar of *Chamaecyparis lawsoniana* and will be referred to hereafter by its cultivar name, 'Edengra 23'. 'Edengra 23' represents a new evergreen coniferous shrub grown for landscape use.

The Inventor discovered the new cultivar in January 2020 as a naturally occurring branch mutation of *Chamaecyparis lawsoniana* 'Ellwoodii' (not patented) that was growing in a container in a production greenhouse in Wezep, The Netherlands.

Asexual propagation of the new cultivar was first accomplished by softwood stem cuttings by the Inventor in Wezep, The Netherlands in January of 2021. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Edengra 23' as a unique cultivar of *Chamaecyparis.*

1. 'Edengra 23' exhibits an upright, columnar and compact plant habit.
2. 'Edengra 23' exhibits foliage that is thick and coarse in texture.
3. 'Edengra 23' exhibits very good growth in peat-free soil.

The parent plant of 'Edengra 23' differs from 'Edengra 23' in having a more open and less compact growth habit and foliage that is finer and thinner, and in growing less well in peat-free soil. 'Edengra 23' can be most closely compared to *Chamaecyparis* cultivars 'Alumii' (not patented) and 'Columnaris' (not patented). Both 'Alumii' and 'Columnaris' are similar to 'Edengra 23' in having green foliage, an upright columnar plant shape, and compact plant habits. Both 'Alumii' and 'Columnaris' differ from 'Edengra 23' in having less compact growth habits and foliage that is finer and thinner in texture.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantarium/

Groen-Direkt and Eden Plants (available in September 2024, but less than year from the filing of this application).

BRIEF DESCRIPTION OF THE DRAWINGS

The accompanying color photographs illustrate the overall appearance and distinct characteristics of the new *Chamaecyparis*. The photographs were taken of a 26-month-old plant of the new cultivar as grown outdoors in 10.5 cm containers in Wezep, The Netherlands.

The photograph in FIG. 1 provides a side view of the overall plant habit of 'Edengra 23'.

Figure 1:
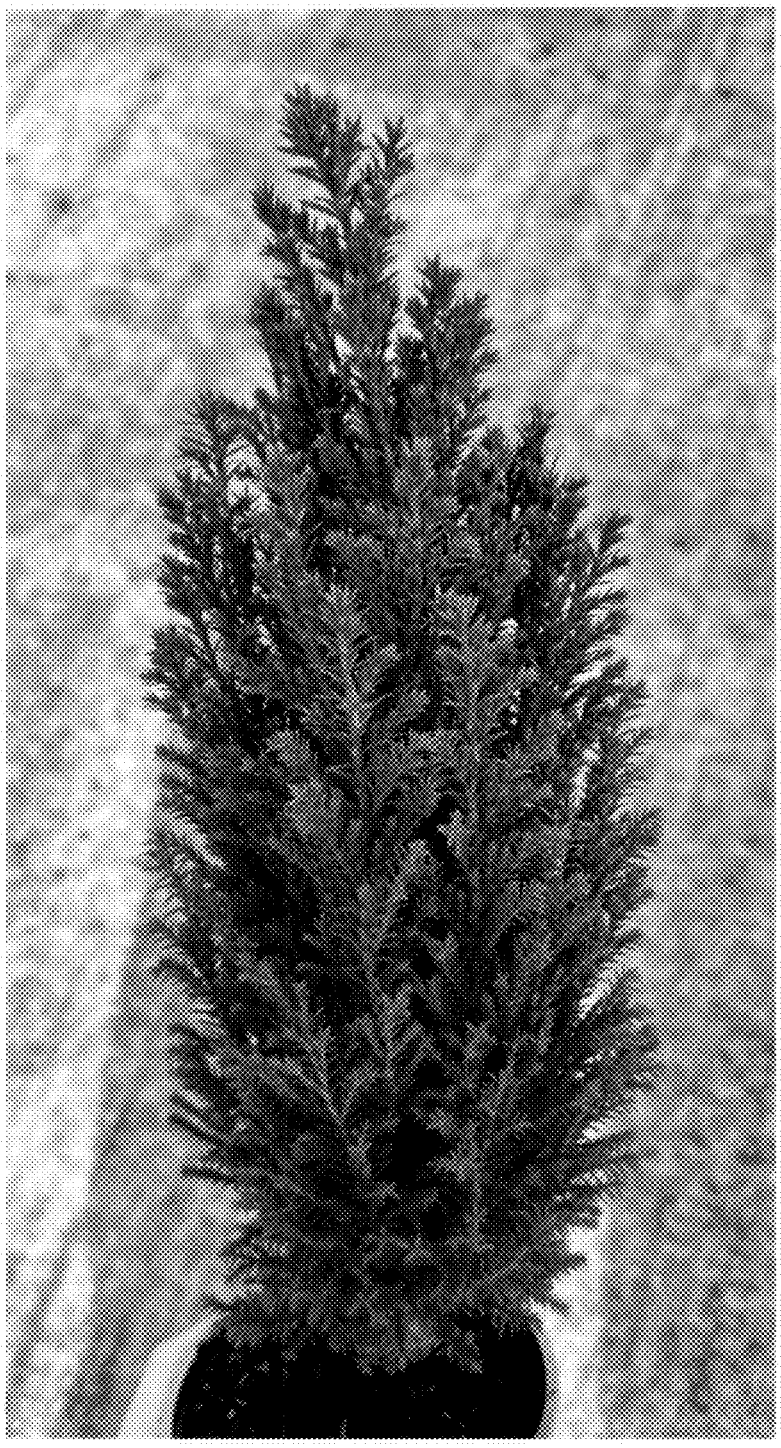
Figure 2:
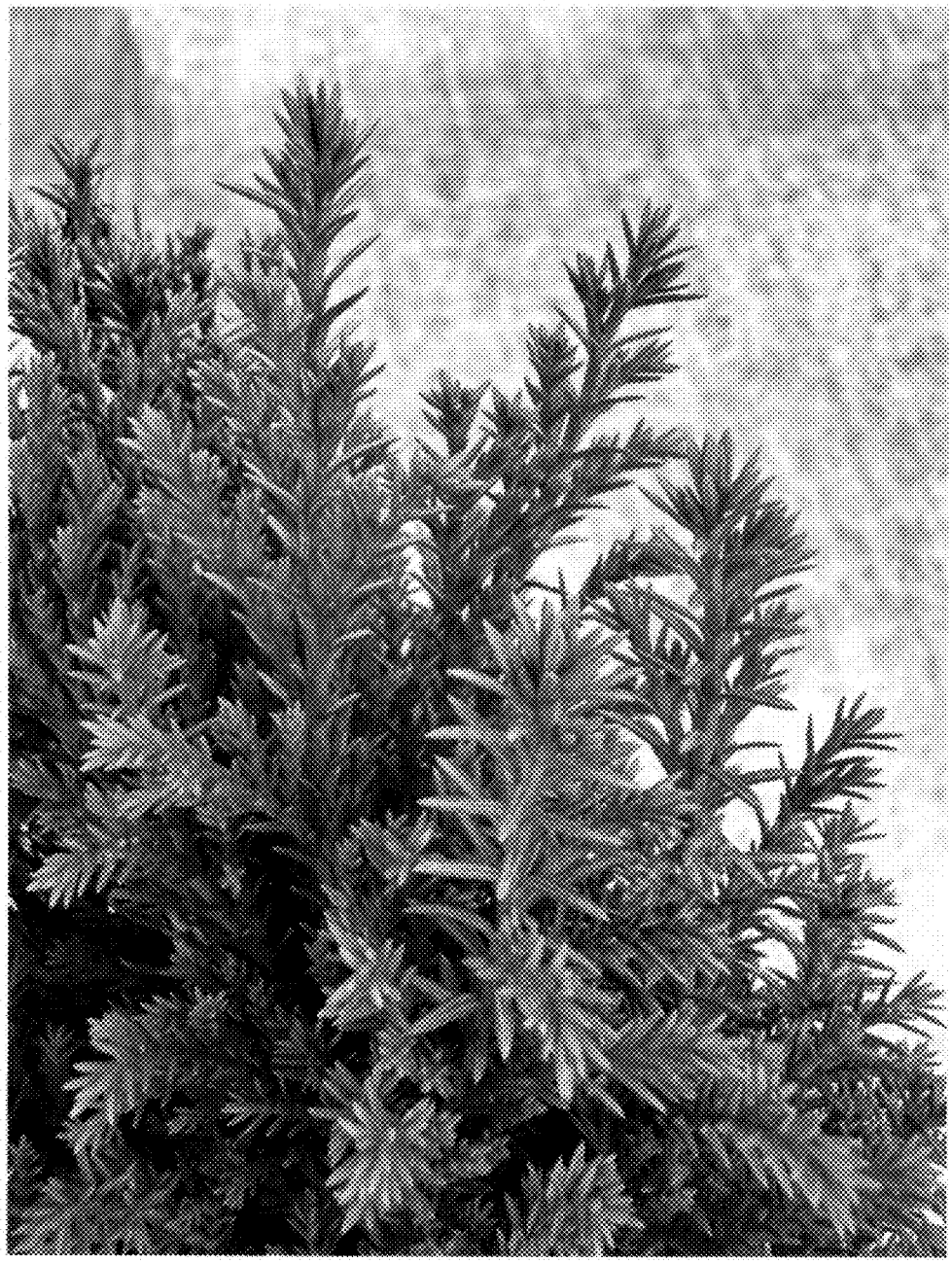

The photograph in FIG. 2 provides a close-up view of the foliage of 'Edengra 23'.

Figure 3:
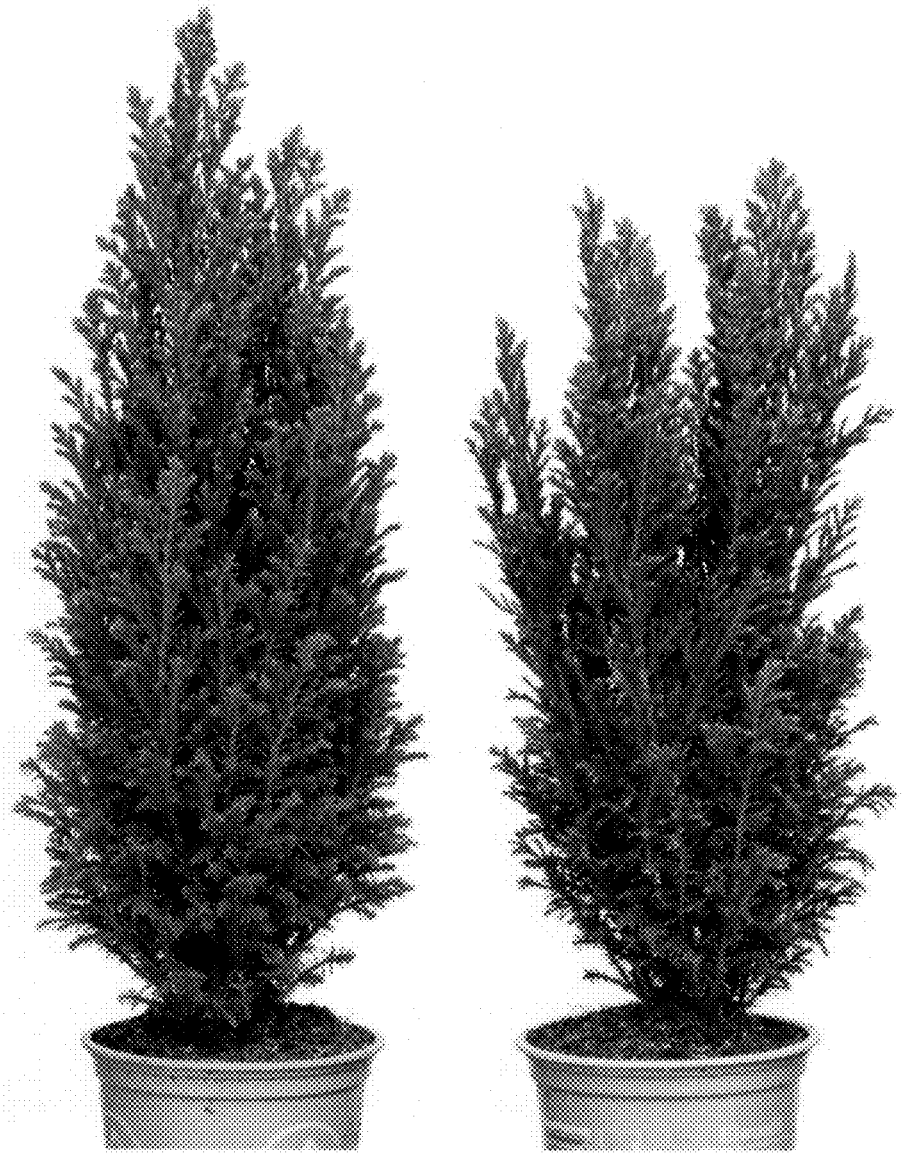

The photograph in FIG. 3 provides a comparison showing the plant habit differences between 'Edengra 23' (shown on the left) and the parent plant 'Ellwoodii' (shown on the right).

The colors in the photographs are as close as possible with the photographic and printing technology utilized and the color values cited in the detailed botanical description accurately describe the colors of the new *Chamaecyparis*.

DETAILED BOTANICAL DESCRIPTION

The following is a detailed description of plants of the new cultivar 26 months in age as grown in 10.5 cm containers outdoors in Wezep, The Netherlands. The phenotype of the new cultivar may vary with variations in environmental, climatic, and cultural conditions, as it has not been tested under all possible environmental conditions. The color determination is in accordance with the 2015, $6^{th}$ edition Colour Chart of The Royal Horticultural Society, London, England, except where general color terms of ordinary dictionary significance are used.

General description:

*Plant type*.—Evergreen coniferous shrub.

*Plant habit*.—Upright, compact, columnar.

*Height and spread*.—An average of 34.5 cm in height and 14.3 cm in spread as a 26-month-old plant a grown in a container, a 3-year-old plant in the landscape it has been observed to reach an average of 1 m in height and 50 cm in width.

*Cold hardiness*.—At least to U.S.D.A. Zone 7.

*Diseases and pests*.—No susceptibility or resistant to pests or diseases has been observed.

*Root description*.—Fibrous.

*Growth rate*.—Vigorous.

*Root development*.—Time for root initiation is an average of 7 weeks, time to produce a fully rooted cutting is an average of 8 months.

*Propagation*.—Softwood stem cuttings.

Branch description:

*Branch shape*.—Rounded.

*Branch size*.—An average of 8.4 cm in length and 2 mm in diameter.

*Branch surface*.—Densely covered with scale-like leaves, slightly glossy.

*Branching*.—Main; 4, lateral; 147 per main branch.

*Branch strength*.—Strong.

*Branch arrangement*.—Alternate.

*Branch aspect*.—Average angle of 17.5°.

*Internode length*.—Average of 7 mm in length.

*Branch color*.—Young; 143C, mature; 165A, older wood and bark; N199C, blotched with N167A.

Foliage description:

*Leaf arrangement*.—Opposite.

*Leaf shape*.—Lanceolate to linear, slightly carinate.

*Leaf division*.—Simple.

*Leaf base*.—Decurrent.

*Leaf apex*.—Apiculate, soft to the touch not sharp.

*Leaf venation*.—Not visible.

*Leaf margins*.—Entire.

*Leaf surface*.—Both surfaces smooth, glabrous and matte.

*Leaf color*.—Young upper surface; 147B, young lower surface; 146B, edged 147B, mature upper surface; 146C, mature lower surface; 145A.

*Leaf aspect*.—Held in an average angle of 60° to lateral branch.

*Leaf size*.—An average of 7 mm in length and 1 mm in width.

*Leaf quantity*.—An average of 475 scale-like leaves per branch.

Cone description: No cones have been observed to date.

It is claimed:

1. A new and distinct cultivar of *Chamaecyparis* plant named 'Edengra 23' substantially as herein illustrated and described.

* * * * *